United States Patent
Lee

(10) Patent No.: US 6,888,001 B2
(45) Date of Patent: May 3, 2005

(54) PYRIDYL ETHERS AND THIOETHERS AS LIGANDS FOR NICOTINIC ACETYLCHOLINE RECEPTOR AND ITS THERAPEUTIC APPLICATION

(76) Inventor: Jung S. Lee, 1034 Ingram Ct., Ambler, PA (US) 19002

( * ) Notice: Subject to any disclaimer, the term of this patent is extended or adjusted under 35 U.S.C. 154(b) by 130 days.

(21) Appl. No.: 10/405,250

(22) Filed: Apr. 2, 2003

(65) Prior Publication Data

US 2003/0207858 A1 Nov. 6, 2003

Related U.S. Application Data

(62) Division of application No. 09/383,142, filed on Aug. 25, 1999, now Pat. No. 6,562,847
(60) Provisional application No. 60/097,853, filed on Aug. 25, 1998.

(51) Int. Cl.[7] .................. H01N 43/40; C07D 401/00
(52) U.S. Cl. .................. 546/276; 546/268; 546/194; 546/278; 514/343
(58) Field of Search .................. 546/276, 268.1, 546/194, 278.4

(56) References Cited

PUBLICATIONS

Holladay et al, J Med. Chem. 41, 407 (1998).*
Decker, et al (1998) Eur. J. Pharmacol, 346, 23.*
Lin et al (1997) J. Med. Chem. 40, 385.*
Basmadjian, G.P. et al., "Design for novel nicotinic acetylcholine receptro agonists with potential antinociceptive activity", Chemical Abstracts, vol. 129, No. 13, Sep. 1998, Columbus, Ohio, US, Abstract No. 156451r.

* cited by examiner

*Primary Examiner*—Paul J. Killos
(74) *Attorney, Agent, or Firm*—John Harbour

(57) ABSTRACT

The present invention provides compounds of the formula:

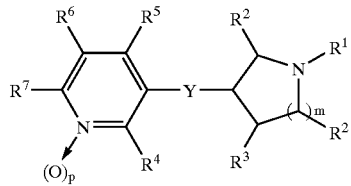

wherein m is 0, 1 or 2; p is 0 or 1; Y is O, S, S(O) or $S(O)_2$ and $R^1$ to $R^7$ are various substituents as selective modulators of the nicotinic acetylcholine receptor useful in the treatment of pain, Alzheimer's disease, memory loss or dementia or loss of motor function.

23 Claims, No Drawings

PYRIDYL ETHERS AND THIOETHERS AS LIGANDS FOR NICOTINIC ACETYLCHOLINE RECEPTOR AND ITS THERAPEUTIC APPLICATION

This application is a division of U.S. pat. application Ser. No. 09/383,142, filed Aug. 25, 1999, now U.S. Pat. No. 6,562,847 and claims the benefit for the purpose of priority of U.S. Prov. Appl. No. 60/097,853 filed Aug. 25, 1998.

FIELD OF THE INVENTION

Briefly, according to the present invention, there are provided selective modulators of nicotinic acetylcholine receptors. More particularly, the present invention provides pyridyl ethers and thioethers as selective nicotinic acetylcholine receptor agonists, partial agonists, antagonists or allosteric binding molecules useful in the treatment of pain, Alzheimer's disease, memory loss or dementia or loss of motor function.

BACKGROUND OF THE INVENTION

Holladay, et. al., in "Identification and Initial Structure-Activity Relationship of (R)-5-(2-Azetidinylmethoxy)-2-chloropyridine (ABT594), a Potent, Orally Active, Non-Opiate Analgesic Agent Acting via Neuronal Nicotinic Acetylcholine Receptors",1998, *J. Med. Chem.*, 41, 407, describe the preparation of ABT594 and its therapeutic utility. A similar disclosure is made by Donnelly-Roberts, et. al., 1998, *J. Pharmacol. Exp. Ther.*, 285, 777 & 787; Decker, et. al., 1998, *Eur. J. Pharmacol.*, 346, 23 and in WO 98/25920; wherein ABT594 is contained within the general structure:

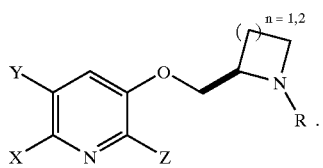

Abreo, et. al., in "Heterocyclic Ether Compounds that enhance Cognitive Function", 1994, W.O. Patent 94/08992, describes the preparation of heterocyclic ether compounds and its therapeutic utility. A similar disclosure is made in Abreo, et. al., 1996, *J. Med. Chem.* 39, 817. Generally, the heterocyclic ether compounds have the structure:

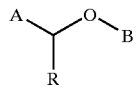

where A is saturated heterocycle, B is unsaturated heterocycle and R is H or $C_{1-6}$alkyl.

Lin, et. al., in "3-Pyridyloxymethyl Heterocyclic ether Compounds useful in Controlling Chemical Synaptic Transmission", 1997, U.S. Pat. No. 5,629,325, describe the preparation of pyridyl ether compound and its therapeutic utility. A similar disclosure is made by Lin, et. al., 1997, *J. Med. Chem.* 40, 385. Generally, the 3-Pyridyloxymethyl heterocyclic ether compounds have the structure:

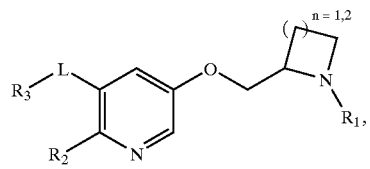

wherein $R_1$ is H or $C_{1-6}$alkyl; $R_2$ is H, F, Cl, vinyl or phenyl; L is a $C_{1-6}$ linking group and $R_3$ is H or $C_{1-6}$alkyl.

Shanklin, et. al., in "Aryloxy and Aryloxyalklazetidines as Antiarrhythmic and Anticonvulsant Agents", 1992, U.S. Pat. No. 5,130,309, describe the preparation of Aryloxy and aryloxyalkyllazetidines and their therapeutic utilities. Generally, the described azetidines have the formula:

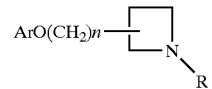

wherein n is 0 to 3, R is H, $C_{1-4}$alkyl or arylalkyl and Ar is phenyl or substituted phenyl.

Cosford, et. al., in "Substituted Pyridine Derivatives, Their Preparation and Their Use as Modulators of Acetylcholine Receptors", 1996, W.O. Patent 96/31475, describe the preparation of substituted pyridine derivatives and its therapeutic utility. Generally, the pyridine derivative have the formula:

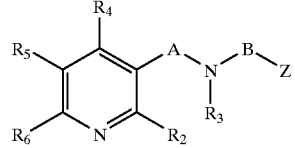

wherein A is 1–6 atoms bridging species linking pyridine and N, B is 1–4 atoms bridging species linking N and Z, Z is H, $C_{1-6}$alkyl, alkynyl or aryl; $R_3$ is H or lower alkyl; and $R_2$, $R_4$, $R_5$, and $R_6$ are H, $C_{1-6}$alkyl, alkynyl , aryl or S-containing groups.

McDonald, et. al., in "Modulators of Acetylcholine Receptors". 1998, U.S. Pat. No. 5,723,477, describe the preparation of C-3 substituted pyridyl compounds and its therapeutic utility. A similar disclosure is made in McDonald, et. al., 1997, U.S. Pat. No. 5,703,100; McDonald, et. al., 1997, U.S. Pat. No. 5,677,459; *Menzaghi*, et. al., 1997, *J. Pharmacol Exp. Ther.* 280, 373, 384, and 393; and *Lloyd*, et. al., 1998, *Life Sci.*, 62, 1601. Generally, the C-3 substituted pyridyl compounds have the formula:

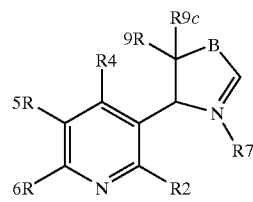

wherein A is 1–3 atom bridging moiety, forming a 5–7 membered ring; B is —O—, —S—, —NR$^{10}$—, —CHR$^{10}$—, =CR$^{10}$— or =N—; $R_2$, $R_4$, $R_5$ and $R_6$ are H, $C_{1-6}$alkyl, aryl, alkynyl, or O—, S—, or N(R)-containing group; and $R_7$ and $R_9$ are H, $C_{1-6}$alkyl, aryl, or alkynyl.

Caldwell, et. al., in "Method for Treatment of Neurodegenerative Diseases" 1993, U.S. Pat. No. 5,212,188, describe the preparation of alkenyl pyridyl compounds and its therapeutic utility. A similar disclosure is made in Bencherif, et. al., 1996 *J. Pharmacol. Exp. Ther.*, 279, 1413 and 1422. Generally, the alkenyl pyridyl compounds have the general formula:

wherein n is 1–5, R is H or $C_{1-5}$alkyl and X is halogen.

Crooks, et. al., in "Nicotinic Receptor Antagonists in the Treatment of Neuropharmacological Disorders" 1997, U.S. Pat. No. 5,691,365, describe the preparation of nicotine analogs and its therapeutic utility. Generally, the nicotinic analogues have the structure:

wherein R is alkyl or branched alkyl with 2–19 carbon atoms, cycloalkyl, aralkyl or alkenyl.

Shen, et. al., in "7-Azabicyclo[2.2.2]-Heptane and -Heptene Derivatives as Cholinergic Receptor Ligands" 1996, W.O. Patent 96/06093, describe the preparation of 7-azabicyclo[2.2.2]-heptane and -heptene derivatives and their therapeutic utilities. A similar disclosure is made by Shen, et. al., 1994, W.O. Patent 94/22868. Generally, the heptane and heptene derivatives have the formula:

wherein $R_1$, $R_2$, $R_3$, $R_4$, $R_5$, $R_6$, and $R_7$ are H, alkyl or an alkyl-heteroatom containing group.

Dybes, et. al., in "Anticoccidal Cyclicaminoethanols and Esters Thereof" 1978, U.S. Pat. No. 4,094,976, describe the preparation of cyclicaminoethanols and esters and their therapeutic utilities. Generally, the cyclicaminoethanols have the formula:

wherein n is 3–5 and R is H or acyl radical.

Caldwell, et. al., in "Method for Treatment of Neurodegenerative Disease" 1993, U.S. Pat. No. 5,214,060 describes the preparation of 3-aminoalkylpyridines and its therapeutic utilities. Generally, the 3-aminoalkylpyrimidines have the formula:

wherein R is $C_{1-7}$alkyl, X is substituent other than H, p is 1–5, m is 0–4 and n is 0–8.

There are two recent reviews on the topic of the nicotinic acetylcholine receptor: Holladay, et. al., in "Neuronal Nicotinic Acetylcholine Receptors as Targets for Drug Discovery" 1997, *J. Med. Chem.*, 40, 4169; and Holladay, et. al., in "Structure-Activity Relationships of Nicotinic Acetylcholine Receptor Agonists as Potential Treatments for Dementia" 1995, *Drug Dev. Res.*, 35, 191.

SUMMARY OF THE INVENTION

There are provided by the present invention selective modulators of the nicotinic acetylcholine receptor of the general formula:

(I)

wherein
   m is selected from 0, 1 or 2;
   p is selected from 0 or 1;
   Y is selected from the group consisting of O, S, S(O) and $S(O)_2$;
   $R^1$ is independently selected from the group consisting of H—, HO—, O—, $C_{1-6}$alkyl—, $C_{2-6}$alkenyl—, $C_{2-6}$alkynyl—, $C_{3-6}$cycloalkyl$C_{1-3}$alkyl—, phenyl$C_{1-3}$alkyl—, —C(O)$C_{1-6}$alkyl, —C(O)phenyl, —C(O)$C_{1-6}$alkylphenyl, —C(O)O$C_{1-6}$alkyl, —C(O)Ophenyl, —C(O)NH$C_{1-6}$alkyl, —C(O)N($C_{1-6}$alkyl)$_2$ and —C(O)NHphenyl; wherein $R^1$ is optionally substituted on a carbon atom with one to three $R^a$ substituents; wherein $R^a$ is independently selected from the group consisting of $C_{1-4}$alkyl, $C_{1-4}$alkoxy, hydroxy$C_{1-4}$alkyl, carbomethoxy, acetoxy, nitro, Cl, Br and F;
   $R^2$ is independently selected from the group consisting of H, $C_{1-6}$alkyl, phenyl and heteroaryl; wherein heteroaryl is as defined below;
   $R^3$ is selected from the group consisting of H, $C_{1-6}$alkyl, Cl, Br and F; with the proviso that if m is 0, then $R^3$ is not Cl, Br or F; and
   $R^4$, $R^5$, $R^6$ and $R^7$ are independently selected from the group consisting of hydrogen and selected radicals; wherein the radicals are selected from the group consisting of:
   a) a trifluoromethyl group: —$CF_3$;
   b) a halogen atom: —Br, —Cl, —F or —I;
   c) a $C_{1-4}$alkoxy radical: —O$C_{1-4}$alkyl; wherein the alkyl is optionally mono- or di-substituted by $R^q$; wherein
      $R^q$ is selected from the group consisting of —OH, —$OCH_3$, —CN, —C(O)$NH_2$, —OC—(O)$NH_2$, CHO, —OC(O)N($CH_3$)$_2$, —$SO_2NH_2$, $SO_2$N($CH_3$)$_2$, —$SOCH_3$, $SO_2CH_3$, —F, —$CF_3$, —COOM$^a$ (wherein M$^a$ is selected from the group consisting of hydrogen, alkali metal, methyl and phenyl), tetrazolyl (wherein the point of attachment is the carbon atom of the tetrazole ring and one of the nitrogen atoms is mono-substituted by M$^a$, as defined previously) and —SO$_3$M$^b$ (wherein M$^b$ is selected from the group consisting of hydrogen and an alkali metal);

d) a hydroxy group: —OH;

e) a carbonyloxy radical: —O(C=O)R$^s$; wherein
R$^s$ is a group selected from the group consisting of C$_{1-4}$alkyl, phenyl and heteroaryl (each of which is optionally mono- or di-substituted with R$^q$, as defined previously); wherein
heteroaryl is a monocyclic aromatic hydrocarbon group having five or six ring atoms, having at least one carbon atom which is the point of attachment, having from one to three carbon atoms replaced by N in the case of six ring atoms, having one carbon atom replaced by O, S or N in the case of five ring atoms and, optionally, having up to three additional carbon atoms replaced by N;

f) a carbamoyloxy radical: —O(C=O)N(R$^y$)R$^z$; wherein
R$^y$ and R$^z$ are independently selected from the group consisting of H, C$_{1-4}$alkyl (optionally mono- or di-substituted by R$^q$, as defined previously), a three to five membered diradical to form a ring wherein R$^y$ and R$^z$ are fused (optionally mono- or di-substituted with R$^q$, as defined previously) and a two to five membered diradical interrupted by —O—, —S—, —S(O)— or —S(O)$_2$— to form a ring wherein R$^y$ and R$^z$ are fused (optionally mono- or di-substituted with R$^q$, as defined previously);

g) a sulfur radical: —(S=(O)$_n$)-R$^s$; wherein n is selected from 0, 1 or 2 and R$^s$ is as defined previously;

h) a sulfamoyl group: —SO$_2$N(R$^y$)R$^z$; wherein R$^y$ and R$^z$ are as defined previously;

i) an azido radical: N$_3$;

j) a formylamino group: —(N—R$^t$)—(C=O)H; wherein R$^t$ is selected from the group consisting of H and C$_{1-4}$alkyl; wherein the alkyl chain is optionally mono- or di-substituted by R$^q$, as defined previously;

k) a (C$_{1-4}$alkyl)carbonylamino radical: —(N—R$^t$)—(C=O)—C$_{1-4}$alkyl; wherein R$^t$ is as defined previously; wherein the alkyl chain is optionally mono-or di-substituted by R$^q$, as defined previously;

l) a (C$_{1-4}$alkoxy)carbonylamino radical: —(N—Rt)—(C=O)—O—C$_{1-4}$alkyl; wherein
R$^t$ is as defined previously; wherein the alkyl chain is optionally mono-substituted by R$^q$, as defined previously;

m) a ureido group: —(N—R$^t$)—(C=O)N(R$^y$)R$^z$; wherein R$^t$, R$^y$ and R$^z$ are as defined previously;

n) a sulfonamido group: —(N—R$^t$)SO$_2$R$^s$; wherein R$^s$ and R$^t$ are as defined previously;

o) a cyano group: —CN;

p) a (C$_{1-4}$alkyl)carbonyl radical; wherein the carbonyl is acetalized: —C(OMe)$_2$C$_{1-4}$ alkyl; wherein the alkyl is optionally mono-substituted by R$^q$, as defined previously;

q) a carbonyl radical: —(C=O)R$^s$; wherein R$^s$ is as defined previously;

r) a hydroximinomethyl radical; wherein the oxygen or carbon atom is optionally substituted with a C$_{1-4}$alkyl group: —CR$^y$=NOR$^z$; wherein R$^y$ and R$^z$ are as defined previously;
with the proviso that R$^y$ and R$^z$ may not be joined together to form a ring;

s) a (C$_{1-4}$alkoxy)carbonyl radical: —(C=O)OC$_{1-4}$alkyl; wherein the alkyl is optionally mono- or di-substituted by R$^q$, as defined previously;

t) a carbamoyl radical: —(C=O)N(R$^y$)R$^z$; wherein R$^y$ and R$^z$ are as defined previously;

u) a N-hydroxycarbamoyl or N(C$_{1-4}$alkoxy)carbamoyl radical in which the nitrogen atom may additionally be substituted by a C$_{1-4}$alkyl group: —(C=O)—N(OR$^y$)R$^z$; wherein R$^y$ and R$^z$ are as defined previously;
with the proviso that R$^y$ and R$^z$ may not be joined together to form a ring;

v) a thiocarbamoyl group: —(C=S)N(R$^y$)R$^z$; wherein R$^y$ and R$^z$ are as defined previously;

w) a carboxyl radical: —COOM$^b$; wherein M$^b$ is as defined previously;

x) a thiocyanate radical: —SCN;

y) a trifluoromethylthio radical: —SCF$_3$;

z) a tetrazolyl radical; wherein the point of attachment is the carbon atom of the tetrazole ring and any one nitrogen atom is mono-substituted by a substituent selected from the group consisting of hydrogen, an alkali metal and a C$_{1-4}$alkyl radical; wherein the C$_{1-4}$alkyl radical is optionally mono- or di-substituted by R$^q$, as defined previously;

aa) an anionic function selected from the group consisting of phosphono [P=O(OM$^b$)$_2$], alkylphosphono [P=O(OM$^b$)—[O(C$_{1-4}$alkyl)]], alkylphosphinyl [P=O(OM$^b$)—(C$_{1-4}$ alkyl)], phosphoramido [P=O(OM$^b$)N(R$^y$)R$^z$ and P=O—(OM$^b$)NHR$^x$], sulfino (SO$_2$M$^b$), sulfo (SO$_3$M$^b$) and acylsulfonamides selected from the group consisting of CONM$^b$SO$_2$R$^x$, CONM$^b$SO$_2$N(R$^y$)R$^z$, SO$_2$NM$^b$CON(R$^y$)R$^z$ and SO$_2$NM$^b$CN; wherein
R$^x$ is selected from the group consisting of phenyl and heteroaryl; wherein heteroaryl is as defined previously and the phenyl and heteroaryl substituents are optionally mono- or di-substituted with R$^q$, as defined previously; M$^b$, R$^y$ and R$^z$ are as defined previously;

ab) a C$_5$–C$_7$ cycloalkyl group; wherein any one carbon atom in the ring is replaced by a heteroatom selected from the group consisting of O, S, NH and N(C$_{1-4}$alkyl); and, in which any one additional carbon atom may be replaced with NH or N(C$_{1-4}$alkyl) and in which at least one carbon atom adjacent to each nitrogen heteroatom has both of its attached hydrogen atoms replaced by one oxygen whereby a carbonyl moiety is formed; with the proviso that there are at most two carbonyl moieties present in the ring;

ac) a C$_2$–C$_4$ alkenyl radical; wherein the radical is optionally mono-substituted by a substituent selected from the group consisting of any one of a) to ab) or is optionally mono-substituted by substituents selected from the group consisting of phenyl, pyridyl, quinoline and isoquinoline; wherein each phenyl, pyridyl, quinoline or isoquinoline substituent is optionally mono- or di-substituted by R$^q$, as defined previously;

ad) a C$_1$–C$_4$ alkyl radical;

ae) a C$_1$–C$_4$ alkyl mono-substituted by a substituent selected from the group consisting of any one of a) to ad);

af) a 2-oxazolidinonyl moiety; wherein the point of attachment is the nitrogen atom of the oxazolidinone ring; wherein the ring oxygen atom is optionally replaced by a heteroatom selected from the group consisting of S and $NR^t$ (wherein $R^t$ is as defined previously) and one of the saturated carbon atoms of the oxazolidinone ring is optionally mono-substituted by a substituent selected from the group consisting of any one of a) to ae);

ag) a $C_2$–$C_4$ alkynyl radical; wherein the radical is independently selected from the group consisting of any one of a) to af) and trialkylsilyl;

ah) phenyl radicals ai) bicyclic radicals; wherein the radical is independently selected from the group consisting of naphthyl, biphenyl, quinoline, indolizine, indole, isoindole, indoline, benzofuran, indazole, benzimidazole, purine, quinolizine, cinnoline, quinoxaline, phthalazine and quinazoline;

aj) heterocyclic radicals; wherein the radical is independently selected from the group consisting of furyl, thienyl, pyrazinyl, pyridazinyl, pyrimidinyl, pyrrolyl, pyrazolyl, imidazolyl, indolyl, thiazolyl, oxazolyl, thiadiazolyl, oxadiazolyl, quinolinyl and isoquinolinyl; and ak) aryl and heteroaryl radicals; wherein the radical is independently selected from the group consisting of any one of ah) through aj);

wherein the radical is substituted with one to two substituents independently selected from the group consisting of $C_1$–$C_6$ alkyl, $C_1$–$C_6$ haloalkyl, $C_1$–$C_6$ alkoxy, $C_1$–$C_6$alkoxy$C_1$–$C_6$alkyl, $C_1$–$C_6$alkoxy$C_1$–$C_6$alkoxy, $C_1$–$C_6$ thioalkyl, halogen, cyano, hydroxy, amino, nitro and $C_1$–$C_6$alkylamino, in which any terminal carbon atom may be replaced by a group selected from the group consisting of carboxyl and $C_2$–$C_6$alkoxycarbonyl;

and pharmaceutically acceptable salts and esters thereof.

DETAILED DESCRIPTION OF THE INVENTION

Relative to the above generic description, certain compounds of the general formula (I) are preferred. Particularly preferred embodiments are those compounds wherein:

$R_1$ is selected from the group consisting of hydrogen, methyl, ethyl, i-propyl, n-propyl, i-butyl, t-butyl, n-butyl, t-pentyl, n-pentyl, cyclohexylmethyl, 3-methyl-1-butyn-3-yl, 4-dimethylaminobenzoyl, 2-hydroxymethylbenzoyl, acetyl, t-butyloxycarbonyl, ethoxycarbonyl, phenoxycarbonyl, 4-nitrophenoxycarbonyl, 4-methoxyphenoxycarbonyl, 4-carbomethoxyphenoxycarbonyl, 4-methylphenoxycarbonyl, 2,6-dimethyl phenoxycarbonyl, 1-acetoxy-1-methyl-ethoxycarbonyl and benzyloxycarbonyl;

$R^2$ is selected from the group consisting of hydrogen, methyl, ethyl, i-propyl, n-propyl, i-butyl, t-butyl, n-butyl, t-pentyl, n-pentyl, phenyl, thienyl and pyridyl;

$R^3$ is selected from the group consisting of hydrogen, Cl, Br, F, methyl, ethyl, i-propyl, n-propyl, i-butyl, t-butyl, n-butyl, t-pentyl and n-pentyl; preferably, $R^3$ is hydrogen;

$R^4$, $R^5$, $R^6$ and $R^7$ are independently selected from the group consisting of hydrogen, —$CH_3$, —$CH_2CH_3$, —$(CH_2)_3CH_3$, —$OCH_3$, —$SCH_3$, —tetrazolyl, —COOH, —$CH_2CONH_2$, —$CH_2CH_2SO_3H$, —$CONH_2$, —$SO_2NH_2$, —$SO_3H$, —$CON(CH_3)_2$, —CN, —$CH_2CN$, —$CH_2SCH_3$, —$CH_2SO_3H$, —$CH_2SOCH_3$, —$CH_2SO_2CH_3$, —$SO_2CH_3$, —$SOCH_3$, —$CH_2OCH_3$, —$N_3$, —$OCOCNH_2$, —OH, —CHO, —$CH_2P(O)(OCH_3)OH$, —$CF_3$, $CH_2OC(O)NH_2$, —$CH_2SO_2NH_2$, —$SCH_2CH_2CN$, Br, Cl, F, —$SCF_3$, —$CH_2SCF_3$, —$SCH_2CF_3$, —$COCH_3$, —CH=NOH, —CONHOH, —$C(S)NH_2$, —$OCOCH_3$, —$NHCOCH_3$, —$NHCO_2CH_3$, —$NHCONH_2$, —$NHSO_2CH_3$, —SCN, —CH=CHCHO, —$SCH_2CH_2OH$, —$CH_2OH$, —CH=$NOCH_2CO_2H$, —$CO_2CH_2CH_2OH$ and —$SO_2NHCH_2CONH_2$; and heteroaryl is selected from the group consisting of pyrrole, pyridine (1N); oxazole, thiazole, oxazine (1N+1O or 1S); thiadiazole (2N+1S); furan (1O); thiophene (1S); pyrazole, imidazole, pyrimidine, pyrazine (2N); triazole, triazine (3N); and tetrazole (4N);

and pharmaceutically acceptable salts and esters thereof.

General Synthetic Methods

Representative compounds of the present invention can be synthesized in accordance with the general synthetic method schemes described below and are illustrated more particularly in the specific synthetic method schemes that follow. Since the schemes are illustrations, the invention should not be construed as being limited by the chemical reactions and conditions expressed. The preparation of the various starting materials used in the schemes is well within the skill of persons versed in the art.

Compounds of the present invention may be made in a preferred one-step reaction scheme that may be preceded or followed by various processes to obtain the desired substituents $R^1$ to $R^7$ and is followed by deprotection of N—$R^{PR}$ to N—$R^1$. The preferred one-step reaction is carried out by the conventional procedure known as the Mitsunobu reaction [O. Mitsunobu, Synthesis, 1(1981)].

Scheme A

Referring to Scheme A, the pyridinyl alcohol Compound A1 is reacted under Mitsunobu conditions with the cyclic alkanol Compound A2 to produce the desired base ring structure of the pyridinyl ethers herein. The reaction takes place in the presence of 1 or 2 equivalents each of triphenylphosine and either diethyl- or diisopropylazodicarboxylate in a suitable solvent such as benzene, toluene or THF at room temperature to reflux overnight. Subsequently, the protecting group $R^{PR}$ is removed and replaced as desired. Suitable protecting groups include $C_{1-8}$ substituted or unsubstituted alkyl; such as, methyl, ethyl or propyl; or $C_{1-8}$ substituted acyl; such as, benzyl carboxylate, allyl carboxylate, acetyl, benzoyl or propanoyl. Many specific protecting groups $R^{PR}$ are included within the definition of $R^1$. Thus, the end product may conveniently have a substitution with $R^1$ which was utilized in the synthesis as a nitrogen protecting group. In such case, deprotection is unnecessary.

Scheme A

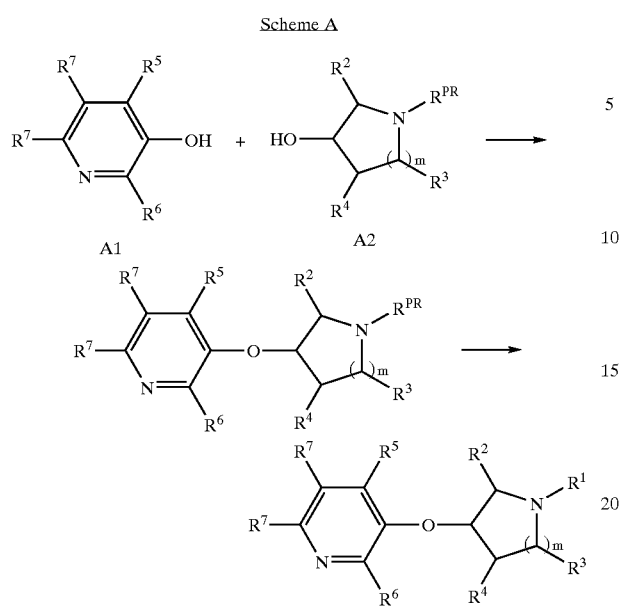

A person skilled in the art can imagine other processes for producing compounds of Formula (I). For example, leaving groups might be employed on analogous starting material Compound A2' wherein the hydroxy on Compound A2' is replaced with with —OMs or —OTs and reacted with Compound A1 to form an ether linkage. The conditions for this reaction are well documented. The thioether linkage; wherein Y is S in Formula (I), can be produced in the manner employing Compound A2' just described using analogous starting material Compound A1', wherein hydroxy is replaced with sulfhydryl. The thioether linkage can be oxidized to $S(O)$ or $S(O)_2$ by the use of oxidizing agents such as the peroxides.

The terms used in describing the invention are commonly used and known to those skilled in the art.

With reference to the above definitions, the term "alkyl" refers to a straight or branched chain aliphatic hydrocarbon radical.

The term "pharmaceutically acceptable salts and esters thereof" refers to those salt and ester forms of the compounds of the present invention which would be apparent to the pharmaceutical chemist, i.e., those which are non-toxic and which would favorably affect the pharmacokinetic properties of said compounds of the present invention. Those compounds having favorable pharmacokinetic properties would be apparent to the pharmaceutical chemist, i.e., those which are non-toxic and which possess such pharmacokinetic properties to provide sufficient palatability, absorption, distribution, metabolism and excretion. Other factors, more practical in nature, which are also important in the selection, are cost of raw materials, ease of crystallization, yield, stability, hygroscopicity, and flowability of the resulting bulk drug.

Examples of suitable salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

Examples of suitable esters include such esters wherein —COOM$^a$, —COOM$^b$ and —COOH are replaced with p-methoxybenzyloxycarbonyl, 2,4,6-trimethylbenzyloxycarbonyl, 9-anthryloxycarbonyl, $CH_3SCH_2COO$—, tetrahydrofur-2-yloxycarbonyl, tetrahydropyran-2-yloxycarbonyl, fur-2-uloxycarbonyl, benzoylmethoxycarbonyl, p-nitrobenzyloxycarbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl or tetrahydropyran-2-yloxycarbonyl.

The preferred compounds of the present invention are listed in Table 1 and include compounds of the formula:

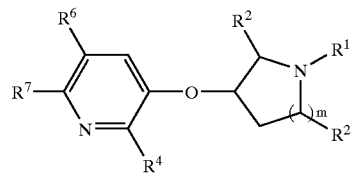

wherein $R^1$ to $R^7$ and m are selected concurrently from the group consisting of:

TABLE 1

| Cpd | m | $R^1$ | $R^2$ | $R^4$ | $R^6$ | $R^7$ |
|---|---|---|---|---|---|---|
| 1$^a$ | 0 | H | H | H | H | H |
| 2$^a$ | 1 | $CH_3$ | H | H | H | H |
| 3$^a$ | 0 | $CH_2CH_3$ | H | H | H | H |
| 4$^a$ | 0 | $CH(CH_3)_2$ | H | H | H | H |
| 5$^a$ | 0 | H | H | H | Br | H |
| 6$^a$ | 0 | H | H | H | H | Cl |
| 7$^a$ | 0 | H | H | Cl | H | H |
| 8$^a$ | 0 | H | H | $CH_3$ | H | H |
| 9$^a$ | 0 | $CH_3$ | H | H | H | Cl |
| 10$^a$ | 0 | $CH_3$ | H | H | Br | H |
| 11$^a$ | 1 | H | H | H | H | H |
| 12$^a$ | 1 | $CH_3$ | H | H | H | H |
| 13$^a$ | 1 | $CH_2CH_3$ | H | H | H | H |
| 14$^a$ | 1 | $CH(CH_3)_2$ | H. | H | H | H |
| 15$^a$ | 1 | H | H | H | Br | H |
| 16$^a$ | 1 | H | H | $CH_3$ | H | H |
| 17$^a$ | 1 | H | H | Cl | H | H |
| 18$^a$ | 1 | H | H | Br | H | H |
| 19$^a$ | 1 | $CH_3$ | H | H | Br | H |
| 20$^a$ | 1 | $CH_3$ | H | H | H | Cl |
| 21$^a$ | 1 | $CH_3$ | $CH_3/CH_3$ | H | H | H |
| 22$^b$ | 1 | H | H | H | H | H |
| 23$^b$ | 1 | $CH_3$ | H | H | H | H |
| 24$^b$ | 1 | $CH_2CH_3$ | H | H | H | H |
| 25$^b$ | 1 | $CH(CH_3)_2$ | H | H | H | H |
| 26$^b$ | 1 | H | H | H | Br | H |
| 27$^b$ | 1 | H | H | $CH_3$ | H | H |
| 28$^b$ | 1 | H | H | Cl | H | H |
| 29$^b$ | 1 | H | H | H | H | $CH_3$ |
| 30$^b$ | 1 | H | H | H | H | Cl |
| 31$^b$ | 1 | $CH_3$ | H | H | Br | H |
| 32$^c$ | 1 | H | H | H | H | H |
| 33$^c$ | 1 | $CH_3$ | H | H | H | H |
| 34$^c$ | 1 | $CH_2CH_3$ | H | H | H | H |
| 35$^c$ | 1 | $CH(CH_3)_2$ | H | H | H | H |
| 36$^c$ | 1 | H | H | H | Br | H |
| 37$^c$ | 1 | H | H | $CH_3$ | H | H |
| 38$^c$ | 1 | H | H | Cl | H | H |
| 39$^c$ | 1 | H | H | H | H | $CH_3$ |
| 40$^c$ | 1 | H | H | H | H | Cl |
| 41$^c$ | 1 | $CH_3$ | H | H | Br | H |
| 42$^b$ | 1 | H | H | H | Br | Cl |
| 43$^b$ | 1 | H | H | H | Ph | H |
| 44$^b$ | 1 | H | H | H | (4-CN)Ph | H |
| 45$^b$ | 1 | H | H | H | (3-OMe)Ph | H |

TABLE 1-continued

| Cpd | m | R¹ | R² | R⁴ | R⁶ | R⁷ |
|---|---|---|---|---|---|---|
| 46[b] | 1 | H | H | H | CCSi(CH₃)₃ | H |
| 47[b] | 1 | H | H | H | CC | H |
| 48[b] | 1 | H | H | H | (3-CN)Ph | H |
| 49[b] | 1 | H | H | H | (4-OMe) | H |
| 50[b] | 1 | H | H | H | (3-Cl)Ph | H |
| 51[b] | 1 | H | H | H | (4-F)Ph | H |
| 52[b] | 1 | H | H | H | (3-Me)Ph | H |
| 53[b] | 1 | H | H | H | (4-SMe)Ph | H |
| 54[b] | 1 | H | H | H | (3-F)Ph | H |
| 55[b] | 1 | H | H | H | (3-Cl-4-F)Ph | H |
| 56[b] | 1 | H | H | H | 4-Pyr | H |
| 57[b] | 1 | H | H | H | Ph | Cl |
| 58[b] | 1 | H | H | H | (4-CN)Ph | Cl |
| 59[b] | 1 | H | H | H | (3-OMe)Ph | Cl |
| 60[b] | 1 | H | H | H | CCSi(CH₃)₃ | Cl |
| 61[b] | 1 | H | H | H | CC | Cl |
| 62[b] | 1 | H | H | H | (3-CN)Ph | Cl |
| 63[b] | 1 | H | H | H | (4-OMe) | Cl |
| 64[b] | 1 | H | H | H | (3-Cl)Ph | Cl |
| 65[b] | 1 | H | H | H | (4-F)Ph | Cl |
| 66[b] | 1 | H | H | H | (3-Me)Ph | Cl |
| 67[b] | 1 | H | H | H | (4-SMe)Ph | Cl |
| 68[b] | 1 | H | H | H | (3-F)Ph | Cl |
| 69[b] | 1 | H | H | H | (3-Cl-4-F)Ph | Cl |
| 70[b] | 1 | H | H | H | 4-Pyr | Cl |
| 71[a] | 2 | H | H | H | H | H |
| 72[a] | 2 | H | H | Cl | H | H |
| 73[a] | 2 | CH₃ | H | H | H | H |
| 74[c] | 2 | H | H | H | H | H |
| 75[c] | 2 | H | H | Cl | H | H |
| 76[c] | 2 | CH₃ | H | H | H | H |
| 77[c] | 2 | H | H | H | Br | H |
| 78[c] | 2 | CH₃ | H | H | Br | H |
| 79[c] | 2 | H | H | H | H | Cl |

[a]Racemate
[b](R)-isomer
[c](S)-isomer

Compounds of Formula (I) may be used in pharmaceutical compositions to treat patients (humans and other primates) with disorders related to the modulation of the nicotinic acetylcholine receptor. Thus, the compounds are effective in the treatment of pain, Alzheimer's disease, memory loss/dementia or loss of motor function. The compounds are particularly effective in the treatment of pain.

The preferred route is oral administration, however compounds may be administered by intravenous infusion or topical administration. Oral doses range from about 0.05 mg to about 100 mg, daily. Some compounds of the invention may be orally dosed in the range from about 0.05 mg to about 50 mg daily, while others may be dosed in the range from about 0.05 mg to about 20 mg daily. Infusion doses can range from about 1.0 to about 1.0×104 mg/min of inhibitor, admixed with a pharmaceutical carrier over a period ranging from several minutes to several days. For topical administration, compounds of Formula (I) may be mixed with a pharmaceutical carrier at a concentration from about 0.1% of drug to about 10% of drug to vehicle.

The pharmaceutical compositions can be prepared using conventional pharmaceutical excipients and compounding techniques. Oral dosage forms may be elixirs, syrups, capsules tablets and the like. Where the typical solid carrier is an inert substance such as lactose, starch, glucose, methyl cellulose, magnesium stearate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Specific Synthetic Methods

In order to illustrate the invention the following examples are included. These examples do not limit the invention. They are only meant to suggest a method of practicing the invention. Those skilled in the art may find other methods of practicing the invention, which are obvious to them. However those methods are deemed to be within the scope of this invention.

Reagents were purchased from Aldrich, Lancaster, Pfaltz & Bauer, TCI America, and used without further purification. ¹H NMR spectra were collected on a Bruker AC-300 spectrometer. Chemical shifts are reported with respect to tetramethylsilane (TMS) $\delta_{H,C}=0.0$ ppm. Spectra were acquired at ambient temperature using DMSO-d₆, CD₃OD or CDCl₃. Mass spectral analyses were performed on a Fisons instrument (Hewlett-Packard HPLC driven electrospray MS instrument). Analytical HPLC analyses were performed on a Hewlett-Packard liquid chromatography system (YMC column, 4 mm×50 mm, 4 mm C₁₈, 1.0 mL/min, 8 min gradient from 95% aqueous media (0.1% TFA) to 95% CH₃CN (0.1% TFA), 220 and 260 nm).

EXAMPLE 1

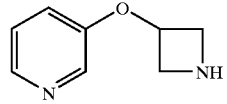

3-(3-Azetidinyloxy)-pyridine

Step (a): 1-t-Butoxycarbonyl-3-hydroxyazetidine

To 2.39 gm (10 mmol) of 1-(diphenylmethyl)-3-hydroxyazetidine in 50 mL of ethanol was added 239 mg of Pd/C. The reaction mixture was then hydrogenated at room temperature for 2 days. After 2 days, the suspension was filtered through celite and washed with H₂O and MeOH. The combined filtrate was concentrated under reduced pressure. To the crude product were then added 50 mL of a solution containing 25 mL of H₂O and 25 mL of dioxane, 2.62 gm (12 mmol) of di-t-butyl dicarbonate, and 2.1 mL (12 mmol) of DIEA at ice-bath temperature. The reaction mixture was slowly warmed to room temperature and allowed to stir at room temperature for 5 h. After 5 h, solvents were removed in vacuo. To the residue were added 100 mL of H₂O and 100 mL of ethyl acetate. After removing the aqueous layer, the organic layer was washed with H₂O (2×50 mL) and concentrated under reduced pressure. The crude product was purified by flash chromatography (2:1, hexane:ethyl acetate) to obtain 560 mg (32%) of a clear oil: ¹H NMR (300 MHz, CD₃OD) δ 4.48 (1H, m), 4.10 (2H, t, J=4.5 Hz), 3.70 (2H, m), 1.43 (9H, s).

Step (b): 3-(1-t-Butoxycarbonyl-3-azetidinyloxy)-pyridine

To 315 mg (1.2 mmol) of PPh₃ in 5 mL of dry THF at −20° C. was added 189 μL (1.2 mmol) of DEAD dropwise. The solution was allowed to stir 10 min. at −20° C. After 10 min, a solution containing 173 mg (1 mmol) of N-Boc-3-hydroxyazetidine and 2 mL of dry THF was added dropwise. The solution was again allowed to stir 10 min at −20° C. After 10 min, to the solution was added 95 mg (1 mmol) of 3-hydroxypyridine at once. The solution was then slowly heated to 70° C. and allowed to stir at 70° C. overnight. Next day, solvent was removed under reduced pressure. The crude product was purified by flash chromatography (2:1, Hexane:Ethyl Acetate) to obtain 160 mg (64% yield) of a yellow oil: ¹H NMR (300 MHz, CD₃OD) δ 8.27 (1H, d, J=4.8 Hz), 8.18 (1H, d, J=2.7 Hz), 7.23 (1H, m), 7.05 (1H, m), 4.92 (1H, m), 4.34–4.00 (2H, AB, J=6.6, 9.7 Hz), 1.45 (9H, s).

Step (c): 3-(3-Azetidinyloxy)-pyridine

To 160 mg (0.64 mmol) of 3-(1-t-butoxycarbonyl-3-azetidinyloxy)-pyridine was added 6 mL of solution containing 3 mL of TFA and 3 mL of $CH_2Cl_2$ at ice-bath temperature. The reaction solution was slowly warmed to room temperature and allowed to stir 50 min at room temperature. After 50 min, solvents were removed in vacuo and the crude product was purified by flash chromatography (9:1: 0.05, $CHCl_3$: MeOH:conc. $NH_4OH$) to obtain 62 mg (67%) of a white solid: $^1$H NMR (300 MHz, $CD_3OD$) δ 8.23 (2H, br s), 7.38 (2H, br d), 5.24 (2H, br s), 4.58 (2H, br d), 4.20 (2H, br d, J=9.8 Hz); Mass spectrum (ESI) m/z 151.7 (M+H$^+$).

EXAMPLE 2

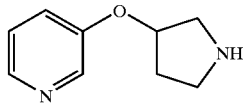

3-(3-Pyrrolidinyloxy)-pyridine

Step (a): 1-t-Butoxycarbonyl-3-hydroxypyrrolidine

To 831 μL (10 mmol) of 3-hydroxypyrrolidine were added 50 mL of a solution containing 25 mL of $H_2O$ and 25 mL of dioxane, 2.62 gm (12 mmol) of di-t-butyl dicarbonate, and 2.1 mL (12 mmol) of DIEA at ice-bath temperature. The reaction mixture was slowly warmed to room temperature and allowed to stir at room temperature for 5 h. After 5 h, solvents were removed in vacuo. To the residue were added 100 mL of $H_2O$ and 100 mL of ethyl acetate. After removing the aqueous layer, the organic layer was washed with $H_2O$ (2×50 mL) and concentrated under reduced pressure. The crude product was purified by flash chromatography (2:1, hexane:ethyl acetate) to obtain 1.6 gm (85.6%) of a clear oil: $^1$H NMR (300 MHz, $CD_3OD$) δ 4.35 (1H, m), 3.41–3.25 (4H, m), 1.95 (2H, m), 1.46 (9H, s).

Step (b): 3-(1-t-Butoxycarbonyl-3-pyrrolidinyloxy)-pyridine

To 755 mg (2.88 mmol) of $PPh_3$ in 15 mL of dry THF at −20° C. was added 453 μL (2.88 mmol) of DEAD dropwise. The solution was allowed to stir 10 min. at −20° C. After 10 min, a solution containing 450 mg (2.4 mmol) of 1-t-butoxycarbonyl-3-hydroxypyrrolidine and 5 mL of dry THF was added dropwise. The solution was again allowed to stir 10 min at −20° C. After 10 min, to the solution was added 229 mg (2.4 mmol) of 3-hydroxypyridine at once. The solution was allowed to stir at room temperature overnight. Next day, solvent was removed under reduced pressure. The crude product was purified by flash chromatography (1:4, hexane: ethyl acetate) to obtain 1.3 gm of the product which contained some triphenyl phospinoxide.

Step (c): 3-(3-Pyrrolidinyloxy)-pyridine

To 1.3 gm of 3-(1-t-butoxycarbonyl-3-pyrrolidinyloxy)-pyridine was added 10 mL of solution containing 5 mL of TFA and 5 mL of $CH_2Cl_2$ at ice-bath temperature. The reaction solution was slowly warmed to room temperature and allowed to stir 50 min at room temperature. After 50 min, solvents were removed in vacuo and the crude product was purified by flash chromatography (9:1: 0.05, $CHCl_3$: MeOH:conc. $NH_4OH$) to obtain 120 mg (30.4% yield in two steps) of a clear oil: $^1$H NMR (300 MHz, $CD_3OD$) δ 8.21 (1H, d, J=2.6 Hz), 8.11 (1H, d, J=4.7 Hz), 7.38 (2H, m), 5.00 (1H, m), 3.13–2.88 (4H, m), 220–1.95 (2H, m); Mass spectrum (ESI) m/z 165.6 (M+H$^+$).

EXAMPLE 3

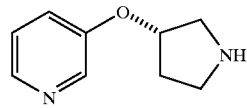

3-(3-(S)-Pyrrolidinyloxy)-pyridine

By the procedure of Example 2, employing the appropriate 3-(R)-hydroxypyrrolidine in place of 3-hydroxypyrrolidine, 3-(3-(S)-pyrrolidinyloxy)-pyridine was produced as a clear oil: $^1$H NMR (300 MHz, $CD_3OD$) δ 8.21 (1H, d, J=2.6 Hz), 8.11 (1H, d, J=3.6 Hz), 7.43–7.34 (2H, m), 5.00 (1H, m), 3.12–2.87 (4H, m), 2,20–1.92 (2H, m); Mass spectrum (ESI) m/z 165.6 (M+H$^+$).

EXAMPLE 4

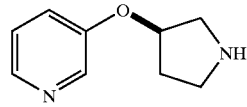

3-(3-(R)-Pyrrolidinyloxy)-pyridine

By the procedure of Example 2, employing the appropriate 3-(S)-hydroxypyrrolidine in place of 3-hydroxypyrrolidine, 3-(3-(R)-pyrrolidinyloxy)-pyridine was produced as a clear oil: $^1$H NMR (300 MHz, $CD_3OD$) δ 8.21 (1H, d, J=2.6 Hz), 8.11 (1H, d, J=4.4 Hz), 7.43–7.34 (2H, m), 5.00 (1H, m), 3.13–2.89 (4H, m), 2,20–1.95 (2H, m); Mass spectrum (ESI) m/z 165.6 (M+H$^+$).

EXAMPLE 5

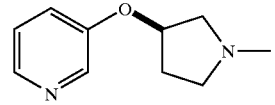

3-(1-Methyl-3-(R)-pyrrolidinyloxy)-pyridine

To 164 mg (1 mmol) of 3-(3-(R)-pyrrolidinyloxy)-pyridine were added 300 mg (10 mmol) of paraformaldehyde, 314 mg (5 mmol) of $NaCNBH_3$, and 5 mL of dry THF at room temperature. To the suspension was added 2 mL of trifluoroacetic acid dropwise. The suspension was allowed to stir at room temperature overnight. Next day, to the suspension was slowly added a mixture containing 20 mL of 4N NaOH and ice-chips. The mixture was then extracted with ethyl acetate (2×40 mL). The combined organic layers were dried over $Na_2SO_4$, and concentrated under reduced pressure. The crude product was purified by flash chromatography (15:1, $CHCl_3$:MeOH) to obtain 9 mg (5%) of a clear oil: $^1$H NMR (300 MHz, $CD_3OD$) δ 8.19 (1H, d, J=1.7 Hz), 8.12 (1H, m). 7.38 (2H, m), 4.99 (1H, m), 2.94–2.80 (3H, m), 2.52–1.93 (3H, m), 2.40 (3H, s); Mass spectrum (ESI) m/z 179.4 (M+H$^+$).

EXAMPLE 6

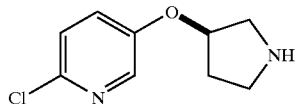

2-Chloro-5-(3-(R)-pyrrolidinyloxy)-pyridine

By the procedure of Example 2, employing the appropriate 3-(S)-hydroxypyrrolidine in place of 3-hydroxypyrrolidine and 2-chloro-5-hydroxypyridine in place of 3-hydroxypyridine, 2-chloro-5-(3-(R)-pyrrolidinyloxy)-pyridine was produced as a clear oil: $^1$H NMR (300 MHz, CD$_3$OD) δ 8.10 (1H, s), 7.50 (1H, dd, J=2.3, 8.8 Hz), 7.40 (1H, d, J=8.8 Hz), 5.28 (1H, s), 3.63–3.31 (4H, m), 2.34 (2H, m).

EXAMPLE 7

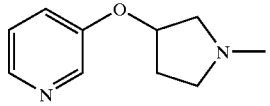

3-(1-Methyl-3-pyrrolidinyloxy)-pyridine

To 629 mg (2.4 mmol) of PPh$_3$ in 13 mL of dry THF at −20° C. was added 378 µL (2.4 mmol) of DEAD dropwise. The solution was allowed to stir 10 min. at −20° C. After 10 min, a solution containing 220 µL (2.0 mmol) of 1-methyl-3-hydroxypyrrolidine and 2 mL of dry THF was added dropwise. The solution was again allowed to stir 10 min at −20° C. After 10 min, to the solution was added 190 mg (2.0 mmol) of 3-hydroxypyridine at once. The solution was allowed to stir at room temperature overnight. Next day, solvent was removed under reduced pressure. The crude product was purified by flash chromatography (9:1, CHCl$_3$:MeOH) to obtain 260 mg (72.9%) of a clear oil: $^1$H NMR (300 MHz, CDCl$_3$) δ 8.26 (1H, d, J=2.6 Hz), 8.20 (1H, d, J=4.2 Hz), 7.22–7.13 (2H, m), 4.85 (1H, m), 2.89–2.76 (3H, m), 2.48–1.95 (3H, m), 2.40 (3H, s); Mass spectrum (ESI) m/z 179.6 (M+H$^+$).

EXAMPLE 8

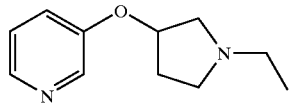

3-(1-Ethyl-3-pyrrolidinyloxy)-pyridine

By the procedure of Example 7, employing the appropriate N-ethyl-3-hydroxypyrrolidine in place of N-methyl-3-hydroxypyrrolidine, 3-(1-ethyl-3-pyrrolidinyloxy)-pyridine was produced as a clear oil; $^1$H NMR (300 MHz, CDCl$_3$) δ 8.27 (1H, d, J=2.6 Hz), 8.20 (1H, d, J=4.0 Hz), 7.22–7.13 (2H, m), 4.87 (1H, m), 2.85 (3H, m), 2.58–1.95 (5H, m), 1.14 (3H, t, J=7.2 Hz); Mass spectrum (ESI) m/z 193.5 (M+H$^+$).

EXAMPLE 9

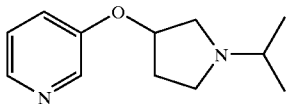

3-(1-Isopropyl-3-pyrrolidinyloxy)-pyridine

By the procedure of Example 7, employing the appropriate N-isopropyl-3-hydroxypyrrolidine in place of N-methyl-3-hydroxypyrrolidine, 3-(1-isopropyl-3-pyrrolidinyloxy)-pyridine was produced as a light yellow oil; $^1$H NMR (300 MHz, CDCl$_3$) δ 8.26 (1H, d, J=2.6 Hz), 8.20 (1H, dd, J=4.3, 1.1 Hz), 7.23–7.13 (2H, m), 4,87 (1H, m), 3.08–1.97 (7H, m), 1.16 (3H, d, J=3.4 Hz), 1.14 (3H, d, J=3.4 Hz); Mass spectrum (ESI) m/z 207.5 (M+H$^+$).

EXAMPLE 10

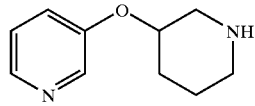

3-(3-Piperidinyloxy)-pyridine
Step (a): 1-t-Butoxycarbonyl-3-hydroxypipendine
To 1.38 gm (10 mmol) of 3-hydroxypyrrolidine were added 50 mL of a solution containing 25 mL of H$_2$O and 25 mL of dioxane, 2.62 gm (12 mmol) of di-t-butyl dicarbonate, and 2.1 mL (12 mmol) of DIEA at ice-bath temperature. The reaction mixture was slowly warmed to room temperature and allowed to stir at room temperature for 5 h. After 5 h, solvents were removed in vacuo. To the residue were added 100 mL of H$_2$O and 100 mL of ethyl acetate. After removing the aqueous layer, the organic layer was washed with H$_2$O (2×50 mL) and concentrated under reduced pressure. The crude product was purified by flash chromatography (1:1, hexane:ethyl acetate) to obtain 1.97 gm (98.0%) of a white solid: $^1$H NMR (300 MHz, CD$_3$OD) 6 3.86–3.50 (3H, m), 2.98–2.81 (2H, m), 1.92–1.73 (2H, m), 1.45 (9H, s), 1.50–1.36 (2H, m).
Step (b): 3-(1-t-Butoxycarbonyl-3-piperidinyloxy)-pyridine
To 629 mg (2.4 mmol) of PPh$_3$ in 13 mL of dry THF at −20° C. was added 378 µL (2.4 mmol) of DEAD dropwise. The solution was allowed to stir 10 min. at −20° C. After 10 min, a solution containing 402 mg (2.0 mmol) of 1-t-butoxycarbonyl-3-hydroxypiperidine and 2 mL of dry THF was added dropwise. The solution was again allowed to stir 10 min at −20° C. After 10 min, to the solution was added 190 mg (2.0 mmol) of 3-hydroxypyridine at once. The solution was allowed to stir at room temperature overnight. Next day, solvent was removed under reduced pressure. The crude product was purified by flash chromatography (1:1, hexane:ethyl acetate) to obtain 130 gm of the product which contained some triphenyl phospinoxide.
Step (c): 3-(3-Piperidinyloxy)-pyridine
To 130 mg of 3-(1-t-butoxycarbonyl-3-piperidinyloxy)-pyridine was added 10 mL of solution containing 5 mL of TFA and 5 mL of CH$_2$Cl$_2$ at ice-bath temperature. The reaction solution was slowly warmed to room temperature and allowed to stir 50 min at room temperature. After 50 min, solvents were removed in vacuo and the crude product was purified by flash chromatography (9:1: 0.05, CHCl$_3$:MeOH:conc. NH$_4$OH) to obtain 83 mg (quantitative yield) of a clear oil: $^1$H NMR (300 MHz, CD$_3$OD) δ 8.27 (1H, d, J=2.7 Hz), 8.13 (1H, d, J=4.0 Hz), 7.49–7.34 (2H, m), 4.52 (1H, m), 3.20–2.80 (4H, m), 2.05–1.55 (4H, m); Mass spectrum (ESI) m/z 179.6 (M+H$^+$).

EXAMPLE 11

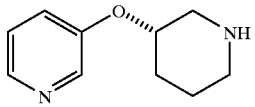

3-(3-(S)-Piperidinyloxy)-pyridine

By the procedure of Example 10, employing the appropriate 3-(R)-hydroxypiperidine in place of 3-hydroxypiperidine, 3-(3-(S)-piperidinyloxy)-pyridine was produced as a clear oil: $^1$H NMR (300 MHz, CD$_3$OD) δ 8.27 (1H, d, J=2.7 Hz), 8.13 (1H, d, J=4.0 Hz), 7.49–7.34 (2H, m), 4.52 (1H, m), 3.20–2.80 (4H, m), 2.05–1.55 (4H, m); Mass spectrum (ESI) m/z 179.6 (M+H$^+$).

EXAMPLE 12

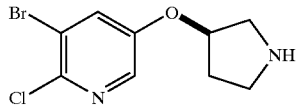

2-Chloro-3-bromo-5-(3-(R)-pyrrolidinyloxy)-pyridine

Step (a): 2-Chloro-3-bromo-5-(1-t-butoxycarbonyl 3-(R)-pyrrolidinyloxy)-pyridine To 3.15 gm (12 mmol) of PPh$_3$ in 100 mL of dry THF at −20° C. was added 1.89 mL (12 mmol) of DEAD dropwise. The solution was allowed to stir 10 min. at −20° C. After 10 min, a solution containing 1.87 gm (10 mmol) of 1-t-butoxycarbonyl-3-(R)-hydroxypyrrolidine in 20 mL of dry THF was added dropwise. The solution was again allowed to stir 10 min at −20° C. After 10 min, to the solution was added 2.08 gm (10 mmol) of 2-chloro-3-bromo-5-hydroxypyridine at once. The solution was allowed to stir at room temperature overnight. Next day, solvent was removed under reduced pressure. The crude product was purified by flash chromatography (3:1, hexane:ethyl acetate) to obtain 3.65 gm (65%) of a foamy residue: $^1$H NMR (300 MHz, CD$_3$OD) δ 8.05 (1H, d, J=2.5 Hz), 7.78 (1H, d, J=2.5 Hz), 5.09 (1H, s), 3.66–3.32 (4H, m), 2.18 (2H, m), 1.46 (9H, s).

Step (b): 2-Chloro-3-bromo-5-(3-(R)-pyrrolidinyloxy)-pyridine

By the procedure of Example 2c, employing the appropriate 2-chloro-3-bromo-5-(1-t-butoxycarbonyl 3-(R)-pyrrolid inyloxy)-pyridine, 2-chloro-3-bromo-5-(3-(R)-pyrrolidinyloxy)-pyridine was produced as a clear oil: $^1$H NMR (300 MHz, CD$_3$OD) δ 8.05 (1H, d, J=2.5 Hz), 7.77 (1H, d, J=2.5 Hz), 5.09 (1H, s), 3.63–3.31 (4H, m), 2.34 (2H, m).

EXAMPLE 13

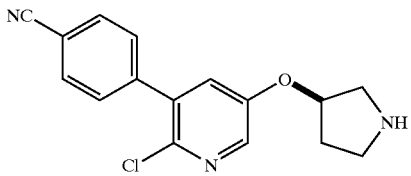

2-Chloro-3-(4-cyano)phenyl-5-(3-(R)-pyrrolidinyloxy)-pyridine

Step (a): 2-Chloro-3-(4-cyano)phenyl-5-(1-t-butoxycarbonyl 3-(R)-pyrrolidinyloxy)-pyridine To 567 mg (1.5 mmol) of 2-chloro-3-bromo-5-(1-t-butoxycarbonyl 3-(R)-pyrrolidinyloxy)-pyridine and 330 mg (2.25 mmol) of 4-cyanophenylboronic acid were added 6 mL of toluene, 6 mL of absolute ethanol, 1.25 mL of [1M] Na$_2$CO$_3$, 63 mg (1.5 mmol) of LiCl and 29 mg (0.025 mmol) of Pd(PPh$_3$)$_4$ under N$_2$ at room temperature. The suspension was slowly heated to 80° C. and allowed to stir overnight at 80° C. Next day, supernatants were collected and concentrated in vacuo. The crude product was purified by flash chromatography (5:2, hexane:ethyl acetate) to obtain 500 mg (83%) of a foamy residue.

Step (b): 2-Chloro-3-(4-cyano)phenyl-5-(3-(R)-pyrrolidinyloxy)-pyridine

By the procedure of Example 2c, employing 490 mg (1.23 mmol) of the appropriate 2-chloro-3-(4-cyano)phenyl-5-(1-t-butoxycarbonyl 3-(R)-pyrrolidinyloxy)-pyridine, 340 mg (75%) of 2-chloro-3-(4-cyano)phenyl-5-(3-(R)-pyrrolidinyloxy)-pyridine was produced as a clear oil: $^1$H NMR (300 MHz, CD$_3$OD) δ 8.11 (1H, d, J=2.9 Hz), 7.84 (2H, d, J=8.2 Hz), 7.66 (2H, d, J=8.3 Hz), 7.46 (1H, d, J=2.9 Hz), 5.07 (1H, s), 3.34–2.91 (4H, m), 2.19–2.04 (2H, m).

EXAMPLE 14

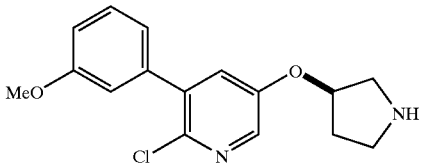

2-Chloro-3-(3-methoxy)phenyl-5-(3-(R)-pyrrolidinyloxy)-pyridine

By the procedure of Example 13, employing 570 mg (1.41 mmol) of the appropriate 2-chloro-3-(3-methoxy)phenyl-5-(1-t-butoxycarbonyl 3-(R)-pyrrolidinyloxy)-pyridine, 380 mg (72%) of 2-chloro-3-(3-methoxy)phenyl-5-(3-(R)-pyrrolidinyloxy)-pyridine was produced as a clear oil: $^1$H NMR (300 MHz, CD$_3$OD) δ 8.05 (1H, d, J=2.9 Hz), 7.38 (2H, m), 7.01 (3H, m), 5.06 (1H, s), 3.83 (3H, s), 3.16–2.90 (4H, m), 2.21–2.03 (2H, m).

EXAMPLE 15

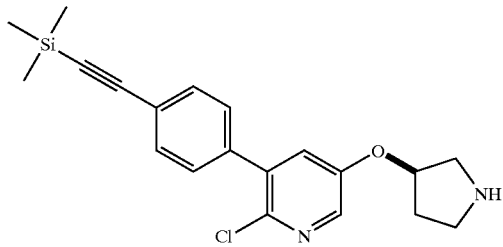

2-Chloro-3-(4-trimethylsilylethynyl)phenyl-5-(3-(R)-pyrrolidinyloxy)-pyridine

Step (a): 2-Chloro-3-(4-trimethylsilylethynyl)phenyl-5-(1-t-butoxycarbonyl-3-(R)-pyrrolidinyloxy)-pyridine To 1.68 gm (4.4 mmol) of 2-chloro-3-bromo-5-(1-t-butoxycarbonyl 3-(R)-pyrrolidinyloxy)-pyridine in 45 mL of dry THF were added 4.5 mL of $Et_3N$, 1.26 mL (8.9 mmol) of trimethylsilylacetylene, 257 mg (0.2 mmol) of $Pd(PPh_3)_4$, and 42 mg (0.2 mmol) of CuI at room temperature. The suspension was slowly heated to 70° C. and allowed to stir 4 h at 70° C. After 4 h, the suspension was cooled to room temperature and allowed to stir 3 days at room temperature. After 3 days, the crude product was concentrated and purified by flash chromatography (6:1, hexane:ethyl acetate) to obtain 1.3 gm (74%) of a yellow oil: $^1$H NMR (300 MHz, $CD_3OD$) δ 8.03 (1H, s), 7.55 (1H, d, J=2.8 Hz), 5.07 (1H, s), 3.65–3.35 (4H, m), 2.16–2.00 (2H, m), 1.46 (9H, s), 0.26 (9H, s).

Step (b):2-Chloro-3-(4-trimethylsilylethynyl)phenyl-5-(3-(R)-pyrrolidinyloxy)-pyridine By the procedure of Example 2c, employing 650 mg (1.66 mmol) of the appropriate 2-chloro-3-(4-trimethylsilylethynyl)phenyl-5-(1-t-butoxycarbonyl-3-(R)-pyrrolidinyloxy)-pyridine, 380 mg (63%) of 2-chloro-3-(4-trimethylsilylethynyl)phenyl-5-(3-(R)-pyrrolidinyloxy)-pyridine was produced as a clear oil: $^1$H NMR (300 MHz, $CD_3OD$) δ 8.03 (1H, d, J=2.9 Hz), 7.55 (1H, d, J=2.9 Hz), 5.09 (1H, s), 3.34–3.11 (4H, m), 2.19–2.10 (2H, m), 0.26 (9H, s).

Biological Protocols

EXAMPLE 1

$α_4β_2$ Nicotinic Acetylcholine Receptor ($α_4β_2$ nAChR)

In Vitro Protocol for Determination of $α_4β_2$ nAChR Binding Potencies of Ligands Binding of $^3$H-cytisine to neuronal nicotinic acetylcholine receptors was accomplished using crude synaptic membrane preparations from rat cerebral cortex, striatum and hippocampus. Either fresh or frozen membranes were homogenized in ~50 volumes of 10 mM HEPES (N-2-Hydroxyethylpiperazine-N'-2-Ethanesulfonic acid, pH 7.4) and centrifuged at 42,000×g. The $P_2$ fraction was resuspended in ~40 volumes of 10 mM HEPES and centrifuged at 42,000×g. This step was repeated and the $P_2$ fraction was resuspended in 25 volumes (e.g. 1 g of original into 25 mL) of a medium comprising $Na^+$-HEPES buffer (10 mM, pH 7.4), 5 mM $MgCl_2$, 0.01% powdered bovine serum albumin (BSA) and 100 mM NaCl. To initiate the binding reaction, test compound (100 µL), Na-HEPES buffered incubation medium (400 µL), $^3$H-cytisine (250 µL) and the suspension of biological membranes (250 µL) were mixed, and then the samples were incubated at 23° C. for 40 minutes. The binding reaction was terminated by filtration using a Brandel Cell Harvester and the amount of bound $^3$H-cytisine for each sample was quantitated using a Wallac LKB 1205 Betaplate liquid scintillation counter. All test compounds were screened at 10 µM in quadruplicate. Nonspecific binding was determined using 10 µM (+)-epibatidine to block all binding of $^3$H-cytisine to the $α_4β_2$ nAChR. The activity of each test compound was calculated as follows. After correcting for nonspecific binding, the percent inhibition of specific binding (total binding minus nonspecific) was calculated. Each active compound was further tested at five concentrations to generate a concentration-inhibition curve. The $IC_{50}$ values were determined using the Prism (GraphPad Software) nonlinear regression program.

EXAMPLE 2

$α_7$ Nicotinic Acetylcholine Receptor ($α_7$nAChR)

In Vitro Protocol for Determination of $α_7$nAChR Binding Potencies of Ligands

Binding of $^3$H-MLA (methylcaconitine) to neuronal nicotinic acetylcholine receptors was accomplished using crude synaptic membrane preparations from rat cerebral cortex, striatum and hippocampus. Either fresh or frozen membranes were homogenized in ~50 volumes of 10 mM HEPES (N-2-Hydroxyethylpiperazine-N'-2-Ethanesulfonic acid, pH 7.4) and centrifuged at 42,000×g. The $P_2$ fraction was resuspended in ~40 volumes of 10 mM HEPES and centrifuged at 42,000×g. This step was repeated and the $P_2$ fraction was resuspended in 25 volumes (e.g. 1 g of original into 25 mL) of a medium comprised of $Na^+$-HEPES buffer (10 mM, pH 7.4), 5 mM $MgCl_2$, 0.01% powdered bovine serum albumin (BSA), and 100 mM NaCl. To initiate the binding reaction, test compound (100 µL), Na-HEPES buffered incubation medium (400 µL), $^3$H-MLA (250 µL) and the suspension of biological membranes (250 µL) were mixed, and then the samples were incubated at 23° C. for 40 minutes., The binding reaction was terminated by filtration using a Brandel Cell Harvester, and the amount of bound $^3$H-MLA for each sample was quantitated using a Wallac LKB 1205 Betaplate liquid scintillation counter. All test compounds were screened at 10 µM in quadruplicate. Nonspecific binding was determined using 10 µM MLA to block all binding of $^3$H-MLA to the $α_7$ nAChR. The activity of each test compound was calculated as follows. After correcting for nonspecific binding, the percent inhibition of specific binding (total binding minus nonspecific) was calculated. Each active compound was further tested at five concentrations to generate a concentration-inhibition curve. The $IC_{50}$ values were determined using the Prism (GraphPad Software) nonlinear regression program.

Biological Data

Table 2 provides the test results from the Biological Protocols for the compounds from Examples 1 to 15 provided by the Specific Synthetic Methods.

TABLE 2

| Ex # | $α_4β_2$ (nM) | $α_7$ (% Inh @ 10 uM) |
|---|---|---|
| 1 | 46[a] | 21 |
| 2 | 209 | −15 |
| 3 | 449 | 5 |
| 4 | 45 | 11 |

TABLE 2-continued

| Ex # | $\alpha_4\beta_2$ (nM) | $\alpha_7$ (% Inh @ 10 uM) |
|---|---|---|
| 5 | 544 | 20 |
| 6 | 466 | 20 |
| 7 | 92 | 22 |
| 8 | 71[a] | 18 |
| 9 | 30[a] | 19 |
| 10 | 204 | 19 |
| 11 | 673 | 86 |
| 12 | 94 | 11 |
| 13 | 22 | 26 |
| 14 | 58 | 33 |
| 15 | 25 | 22 |

[a] % Inhibition at 10 μM

What is claimed is:
1. A compound of the general formula:

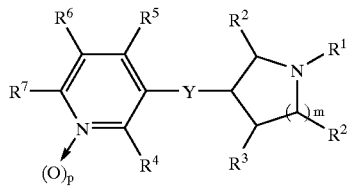

wherein m is selected from 0, 1 or 2;

p is selected from 0 or 1;

Y is selected from the group consisting of O, S, S(O) and S(O)$_2$;

$R^1$ is independently selected from the group consisting of H—, HO—, O—, $C_{1-6}$alkyl—, $C_{2-6}$alkenyl—, $C_{2-6}$alkynyl—, $C_{3-6}$cycloalkyl$C_{1-3}$alkyl—, phenyl$C_{1-3}$alkyl—, —C(O)$C_{1-6}$alkyl, —C(O)phenyl, —C(O)$C_{1-6}$alkylphenyl, —C(O)O$C_{1-6}$alkyl, —C(O)Ophenyl, —C(O)NH$C_{1-6}$alkyl, —C(O)N($C_{1-6}$alkyl)$_2$ and —C(O)NHphenyl; wherein $R^1$ is optionally substituted on a carbon atom with one to three $R^a$ substituents; wherein $R^a$ is independently selected from the group consisting of $C_{1-4}$alkyl, $C_{1-4}$alkoxy, hydroxy$C_{1-4}$alkyl, carbomethoxy, acetoxy, nitro, Cl, Br and F;

$R^2$ is independently selected from the group consisting of H, $C_{1-6}$alkyl, phenyl and heteroaryl; wherein heteroaryl is as defined below;

$R^3$ is selected from the group consisting of H, $C_{1-6}$alkyl, Cl, Br and F; with the proviso that if m is 0, then $R^3$ is not Cl, Br or F; and $R^4$, $R^5$, $R^6$ and $R^7$ are independently selected from the group consisting of hydrogen and at least one is a selected radicals; wherein the radicals are selected from the group consisting of:

g) a sulfur radical: —(S=(O)$_n$)-$R^s$; wherein n is selected from 0, 1 or 2 and $R^s$ is as defined previously;

$R^s$ is a group selected from the group consisting of $C_{1-4}$ alkyl, phenyl and heteroaryl (each of which is optionally mono- or di-substituted with $R^q$, as defined previously); wherein
heteroaryl is a monocyclic aromatic hydrocarbon group having five or six ring atoms, having at least one carbon atom which is the point of attachment, having from one to three carbon atoms replaced by N in the case of six ring atoms, having one carbon atom replaced by O, S or N in the case of five ring atoms and, optionally, having up to three additional carbon atoms replaced by N;

$R^q$ is selected from the group consisting of —OH, —OCH$_3$, —CN, —C(O)NH$_2$, —OC—(O)NH$_2$, CHO, —OC(O)N(CH$_3$)$_2$, —SO$_2$NH$_2$, SO$_2$N(CH$_3$)$_2$, —SOCH$_3$, SO$_2$CH$_3$, —F, —CF$_3$, —COOM$^a$ (wherein M$^a$ is selected from the group consisting of hydrogen, alkali metal, methyl and phenyl), tetrazolyl (wherein the point of attachment is the carbon atom of the tetrazole ring and one of the nitrogen atoms is mono-substituted by M$^a$, as defined previously) and —SO$_3$M$^b$ (wherein M$^b$ is selected from the group consisting of hydrogen and an alkali metal);

h) a sulfamoyl group: —SO$_2$N($R^y$)$R^z$; wherein $R^y$ and $R^z$ are as defined previously;

$R^y$ and $R^z$ are independently selected from the group consisting of H, $C_{1-4}$alkvl (optionally mono- or di-substituted by $R^q$, as defined previously), a three to five membered diradical to form a ring wherein $R^y$ and $R^z$ are fused (optionally mono- or di-substituted with $R^q$, as defined previously) and a two to five membered diradical interrupted by —O—, —S—, —S(O)— or —S(O)$_2$— to form a ring wherein $R^y$ and $R^z$ are fused (optionally mono- or di-substituted with $R^q$, as defined previously);

n) a sulfonamido group: —(N—$R^t$)SO$_2$$R^s$; wherein $R^s$ and $R^t$ are as defined previously;

$R^t$ is selected from the group consisting of H and $C_{1-4}$alkyl; wherein the alkyl chain is optionally mono- or di-substituted by $R^q$, as defined previously:

v) a thiocarbamoyl group: —(C=S)N($R^y$)$R^z$; wherein $R^y$ and $R^z$ are as defined previously;

x) a thiocyanate radical: —SCN;

y) a trifluoromethylthio radical: —SCF$_3$;

z) a tetrazolyl radical; wherein the point of attachment is the carbon atom of the tetrazole ring and any one nitrogen atom is mono-substituted by a substituent selected from the group consisting of hydrogen, an alkali metal and a $C_{1-4}$alkyl radical; wherein the $C_{1-4}$alkyl radical is optionally mono- or di-substituted by $R^q$, as defined previously;

ac) a $C_2$–$C_4$ alkenyl radical; wherein the radical is optionally mono-substituted by a substituent selected from the group consisting of any one of g), h), n), x), y) and z) or is mono-substituted by substituents selected from the group consisting of phenyl, pyridyl, quinoline and isoquinoline; wherein each phenyl, pyridyl, quinoline or isoquinoline substituent is optionally mono- or di-substituted by $R^q$, as defined previously;

ae) a $C_1$–$C_4$ alkyl mono-substituted by a substituent selected from the group consisting of any one of g), h), n), x), y) and z);

ag) a $C_2$–$C_4$ alkynyl radical; wherein the radical is mono-substituted by a substituents selected from the group consisting of any one of g), h), n), x), y) and z) and trialkylsilyl;

ah) phenyl radicals ai) bicyclic radicals; wherein the radical is independently selected from the group consisting of naphthyl, biphenyl, quinoline, indolizine, indole, isoindole, indoline, benzofuran, indazole, benzimidazole, purine, quinolizine, cinnoline, quinoxaline, phthalazine and quinazoline;

aj) heterocyclic radicals; wherein the radical is independently selected from the group consisting of furyl, thienyl, pyrazinyl, pyridazinyl, pyrimidinyl, pyrrolyl, pyrazolyl, imidazolyl, indolyl, thiazolyl, oxazolyl, thiadiazolyl, oxadiazolyl, quinolinyl and isoquinolinyl; and ak) aryl and heteroaryl radicals; wherein the radical is independently selected from the group consisting of any one of ah) through aj); wherein the radical is substituted with one or two substituents independently selected from the group consisting of $C_1$–$C_6$ alkyl, $C_1$–$C_6$ haloalkyl, $C_1$–$C_6$ alkoxy, $C_1$–$C_6$ alkoxy$C_1$–$C_6$ alkyl, $C_1$–$C_6$ alkoxy$C_1$–$C_6$ alkoxy, $C_1$–$C_6$ thioalkyl, halogen, cyano, hydroxy, amino, nitro and $C_1$–$C_6$ alkylamino, in which any terminal carbon atom may be replaced by a group selected from the group consisting of carboxyl and $C_2$–$C_6$ alkoxycarbonyl;

and pharmaceutically acceptable salts and esters thereof.

2. The compound of claim 1 wherein the compound is a selective modulator of the nicotinic acetylcholine receptor.

3. The compound of claim 1 wherein the compound is an antagonist of the nicotinic acetylcholine receptor.

4. The compound of claim 1 wherein the compound is an agonist of the nicotinic acetylcholine receptor.

5. The compound of claim 1 wherein
$R^1$ is selected from the group consisting of hydrogen, methyl, ethyl, i-propyl, n-propyl, i-butyl, t-butyl, n-butyl, t-pentyl, n-pentyl, cyclohexylmethyl, 3-methyl-1-butyn-3-yl, 4-dimethylaminobenzoyl, 2-hydroxymethylbenzoyl, acetyl, t-butyloxycarbonyl, ethoxycarbonyl, phenoxycarbonyl, 4-nitrophenoxycarbonyl, 4-methoxyphenoxycarbonyl, 4-carbomethoxyphenoxycarbonyl, 4-methylphenoxycarbonyl, 2,6-dimethylphenoxycarbonyl, 1-acetoxy-1-methyl-ethoxycarbonyl and benzyloxycarbonyl.

6. The compound of claim 1 wherein
$R^2$ is selected from the group consisting of hydrogen, methyl, ethyl, i-propyl, n-propyl, i-butyl, t-butyl, n-butyl, t-pentyl, n-pentyl, phenyl, thienyl and pyridyl.

7. The compound of claim 1 wherein
$R^3$ is selected from the group consisting of hydrogen, Cl, Br, F, methyl, ethyl, i-propyl, n-propyl, i-butyl, t-butyl, n-butyl, t-pentyl and n-pentyl.

8. The compound of claim 1 wherein $R^3$ is hydrogen.

9. The compound of claim 1 wherein
$R^4$, $R^5$, $R^6$ and $R^7$ are independently selected from the group consisting of hydrogen, —$CH_3$, —$CH_2CH_3$, —$(CH_2)_3CH_3$, —$OCH_3$, —$SCH_3$, —tetrazolyl, —COOH, —$CH_2CONH_2$, —$CH_2CH_2SO_3H$, —$CONH_2$, —$SO_2NH_2$, —$SO_3H$, —$CON(CH_3)_2$, —CN, —$CH_2CN$, —$CH_2SCH_3$, —$CH_2SO_3H$, —$CH_2SOCH_3$, —$CH_2SO_2CH_3$, —$SO_2CH_3$, —$SOCH_3$, —$CH_2OCH_3$, —$N_3$, —$OCOCNH_2$, —OH, —CHO, —$CH_2P(O)(OCH_3)OH$, —$CF_3$, $CH_2OC(O)NH_2$, —$CH_2SO_2NH_2$, —$SCH_2CH_2CN$, Br, Cl, F, —$SCF_3$, —$CH_2SCF_3$, —$SCH_2CF_3$, —$COCH_3$, —CH=NOH, —CONHOH, —C(S)$NH_2$, —$OCOCH_3$, —$NHCOCH_3$, —$NHCO_2CH_3$, —$NHCONH_2$, —$NHSO_2CH_3$, —SCN, —CH=CHCHO, —$SCH_2CH_2OH$, —$CH_2OH$, —CH=$NOCH_2CO_2H$, —$CO_2CH_2CH_2OH$ and —$SO_2NHCH_2CONH_2$.

10. The compound of claim 1 wherein heteroaryl is selected from the group consisting of pyrrole, pyridine, oxazole, thiazole, oxazine, thiadiazole, furan, thiophene, pyrazole, imidazole, pyrimidine, pyrazine, triazole, triazine and tetrazole.

11. The compound of claim 1 wherein said pharmaceutically acceptable salt is selected from the group consisting of hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

12. The compound of claim 1 wherein the pharmaceutically acceptable ester is an ester wherein —COOM$^a$, —COOM$^b$ and —COOH are selected from the group consisting of p-methoxybenzyloxycarbonyl, 2,4,6-trimethylbenzyloxycarbonyl, 9-anthryloxycarbonyl, $CH_3SCH_2COO$—, tetrahydrofur-2-yloxycarbonyl, tetrahydropyran-2-yloxycarbonyl, fur-2-uloxycarbonyl, benzoylmethoxycarbonyl, p-nitrobenzyloxycarbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl or tetrahydropyran-2-yloxycarbonyl.

13. The compound of claim 1 wherein the compound has the general formula:

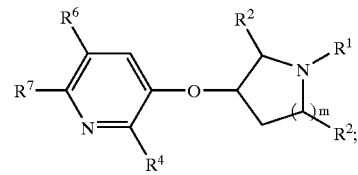

wherein $R^1$ to $R^7$ and m are selected concurrently from the group consisting of:

| Cpd | m | $R^1$ | $R^2$ | $R^4$ | $R^6$ | $R^7$ |
|---|---|---|---|---|---|---|
| 44$^b$ | 1 | H | H | H | (4-CN)Ph | H |
| 45$^b$ | 1 | H | H | H | (3-OMe)Ph | H |
| 46$^b$ | 1 | H | H | H | CCSi(CH$_3$)$_3$ | H |
| 48$^b$ | 1 | H | H | H | (3-CN)Ph | H |
| 50$^b$ | 1 | H | H | H | (3-Cl)Ph | H |
| 51$^b$ | 1 | H | H | H | (4-F)Ph | H |
| 52$^b$ | 1 | H | H | H | (3-Me)Ph | H |
| 53$^b$ | 1 | H | H | H | (4-SMe)Ph | H |
| 54$^b$ | 1 | H | H | H | (3-F)Ph | H |
| 55$^b$ | 1 | H | H | H | (3-Cl-4-F)Ph | H |
| 56$^b$ | 1 | H | H | H | 4-Pyr | H |
| 57$^b$ | 1 | H | H | H | Ph | Cl |
| 58$^b$ | 1 | H | H | H | (4-CN)Ph | Cl |
| 59$^b$ | 1 | H | H | H | (3-OMe)Ph | Cl |
| 60$^b$ | 1 | H | H | H | CCSi(CH$_3$)$_3$ | Cl |
| 62$^b$ | 1 | H | H | H | (3-CN)Ph | Cl |
| 64$^b$ | 1 | H | H | H | (3-Cl)Ph | Cl |
| 65$^b$ | 1 | H | H | H | (4-F)Ph | Cl |
| 66$^b$ | 1 | H | H | H | (3-Me)Ph | Cl |
| 67$^b$ | 1 | H | H | H | (4-SMe)Ph | Cl |
| 68$^b$ | 1 | H | H | H | (3-F)Ph | Cl |
| 69$^b$ | 1 | H | H | H | (3-Cl-4-F)Ph | Cl |
| 70$^b$ | 1 | H | H | H | 4-Pyr | Cl |

$^a$Racemate

-continued

| Cpd | m | R¹ | R² | R⁴ | R⁶ | R⁷ |
|---|---|---|---|---|---|---|
| b(R)-isomer | | | | | | |
| c(S)-isomer | | | | | | |

14. The compound of claim 1 wherein the compound is selected from the group consisting of:

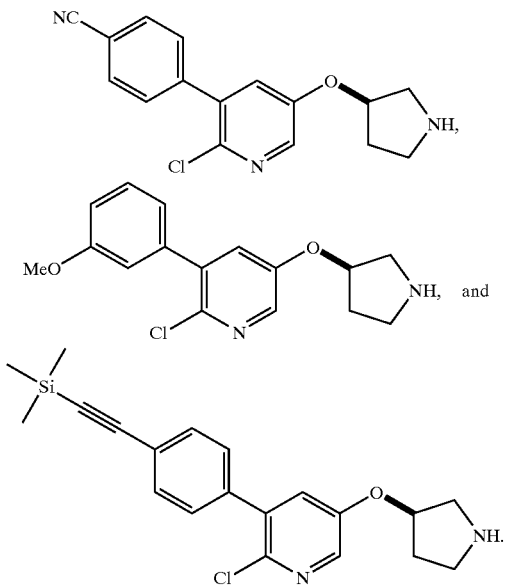

15. A method for treating a condition or disease the pathogenesis of which may be regulated by modulation of the nicotinic acetylcholine receptor which comprises the step of administering to a patient suffering from such a condition or disease an effective amount of a compound of the general formula:

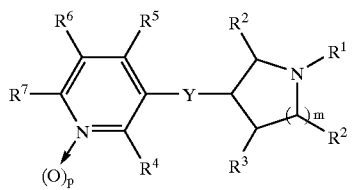

wherein
m is selected from 0, 1 or 2;
p is selected from 0 or 1;
Y is selected from the group consisting of O, S, S(O) and S(O)$_2$;
R¹ is independently selected from the group consisting of H—, HO—, O—, $C_{1-6}$alkyl—, $C_{2-6}$alkenyl—, $C_{2-6}$alkynyl—, $C_{3-6}$cycloalkyl$C_{1-3}$alkyl—, phenyl$C_{1-3}$alkyl—, —C(O)$C_{1-6}$alkyl, —C(O)phenyl, —C(O)$C_{1-6}$alkylphenyl, —C(O)O$C_{1-6}$alkyl, —C(O)Ophenyl, —C(O)NH$C_{1-6}$alkyl, —C(O)N($C_{1-6}$alkyl)$_2$ and —C(O)NHphenyl; wherein R¹ is optionally substituted on a carbon atom with one to three R$^a$ substituents; wherein R$^a$ is independently selected from the group consisting of $C_{1-4}$alkyl, $C_{1-4}$alkoxy, hydroxy$C_{1-4}$alkyl, carbomethoxy, acetoxy, nitro, Cl, Br and F;
R² is independently selected from the group consisting of H, $C_{1-6}$alkyl, phenyl and heteroaryl; wherein heteroaryl is as defined below;
R³ is selected from the group consisting of H, $C_{1-6}$alkyl, Cl, Br and F; with the proviso that if m is 0, then R³ is not Cl, Br or F; and
R⁴, R⁵, R⁶ and R⁷ are independently selected from the group consisting of hydrogen and at least one is a selected radicals; wherein the radicals are selected from the group consisting of:
g) a sulfur radical: —(S=(O)$_n$)R$^z$; wherein n is selected from 0, 1 or 2 and R$^s$ is as defined previously;
R$^s$ is a group selected from the group consisting Of $C_{1-4}$ alkyl, phenyl and heteroaryl (each of which is optionally mono- or di-substituted with R$^q$, as defined previously; wherein
heteroaryl is a monocyclic aromatic hydrocarbon group) having five or six ring atoms, having at least one carbon atom which is the point of attachment, having from one to three carbon atoms replaced by N in the case of six ring atoms, having one carbon atom replaced by O, S or N in the case of five ring atoms and, optionally, having up to three additional carbon atoms replaced by N;
R$^q$ is selected from the group consisting of —OH, —OCH$_3$, —CN, —C(O)NH$_2$, —OC—(O)NH$_2$, CHO, —OC(O)N(CH$_3$)$_2$, —SO$_2$NH$_2$, SO$_2$N(CH$_3$)$_2$, —SOCH$_3$, SO$_2$CH$_3$, —F, —CF$_3$, —COOM$^a$ (wherein M$^a$ is selected from the group consisting of hydrogen, alkali metal, methyl and phenyl), tetrazolyl (wherein the point of attachment is the carbon atom of the tetrazole ring and one of the nitrogen atoms is mono-substituted by M$^a$, as defined Previously) and —SO$_3$M$^b$ (wherein M$^b$ is selected from the group consisting of hydrogen and an alkali metal);
h) a sulfamoyl group: —SO$_2$N(R$^y$)R$^z$; wherein R$^y$ and R$^z$ are as defined previously;
R$^y$ and R$^z$ are independently selected from the group consisting of H, $C_{1-4}$alkyl (optionally mono- or di-substituted by R$^q$, as defined Previously), a three to five membered diradical to form a ring wherein R$^y$ and R$^z$ are fused (optionally mono- or di-substituted with R$^q$, as defined previously) and a two to five membered diradical interrupted by —O—, —S—, —S(O)— or —S(O)$_2$— to form a ring wherein R$^y$ and R$^z$ are fused (optionally mono- or di-substituted with R$^q$, as defined previously);
n) a sulfonamido group: —(N—R$^t$)SO$_2$R$^s$; wherein R$^s$ and R$^t$ are as defined previously;
R$^t$ is selected from the group consisting of H and $C_{1-4}$alkyl; wherein the alkyl chain is optionally mono- or di-substituted by R$^q$, as defined previously;
v) a thiocarbamoyl group: —(C=S)N(R$^y$)R$^z$; wherein R$^y$ and R$^z$ are as defined previously;
x) a thiocyanate radical: —SCN;
y) a trifluoromethylthio radical: —SCF$_3$;
z) a tetrazolyl radical; wherein the point of attachment is the carbon atom of the tetrazole ring and any one nitrogen atom is mono-substituted by a substituent selected from the group consisting of hydrogen, an alkali metal and a $C_{1-4}$alkyl radical; wherein the $C_{1-4}$alkyl radical is optionally mono- or di-substituted by R$^q$, as defined previously;
ac) a $C_2$–$C_4$ alkenyl radical; wherein the radical is mono-substituted by a substituent selected from the group consisting of any one of g), h), n), x), y) and z )or is mono-substituted by substituents selected from the group consisting of phenyl, pyridyl, quinoline and isoquinoline; wherein each phenyl, pyridyl, quinoline or isoquinoline substituent is optionally mono- or di-substituted by $R^q$, as defined previously;

ae) a $C_1$–$C_4$ alkyl mono-substituted by a substituent selected from the group consisting of any one of g), h), n), x), y) and z);

ag) a $C_2$–$C_4$ alkynyl radical; wherein the radical is mono-substituted by a substituents selected from the group consisting of any one of g), h), n), x), y) and z) and trialkylsilyl;

ah) phenyl radicals ai) bicyclic radicals; wherein the radical is independently selected from the group consisting of naphthyl, biphenyl, quinoline, indolizine, indole, isoindole, indoline, benzofuran, indazole, benzimidazole, purine, quinolizine, cinnoline, quinoxaline, phthalazine and quinazoline;

aj) heterocyclic radicals; wherein the radical is independently selected from the group consisting of furyl, thienyl, pyrazinyl, pyridazinyl, pyrimidinyl, pyrrolyl, pyrazolyl, imidazolyl, indolyl, thiazolyl, oxazolyl, thiadiazolyl, oxadiazolyl, quinolinyl and isoquinolinyl; and ak) aryl and heteroaryl radicals; wherein the radical is independently selected from the group consisting of any one of ah) through aj); wherein the radical is substituted with one or two substituents independently selected from the group consisting of $C_1$–$C_6$ alkyl, $C_1$–$C_6$ haloalkyl, $C_1$–$C_6$ alkoxy, $C_1$–$C_6$alkoxy$C_1$–$C_6$alkyl, $C_1$–$C_6$alkoxy$C_1$–$C_6$alkoxy, $C_1$–$C_6$ thioalkyl, halogen, cyano, hydroxy, amino, nitro and $C_1$–$C_6$alkylamino, in which any terminal carbon atom may be replaced by a group selected from the group consisting of carboxyl and $C_2$–$C_6$alkoxycarbonyl;

and pharmaceutically acceptable salts and esters thereof.

16. The method of claim 15 wherein the compound is a selective modulator of the nicotinic acetylcholine receptor.

17. The method of claim 15 wherein the compound is an antagonist of the nicotinic acetylcholine receptor.

18. The method of claim 15 wherein the compound is an agonist of the nicotinic acetylcholine receptor.

19. The method of claim 15 wherein the condition is acute or chronic pain and the patient is in need of analgesia.

20. The method of claim 15 wherein the condition or disease is Alzheimer's disease, memory loss or dementia or loss of motor function.

21. A pharmaceutical composition for treating a condition or a disease the pathogenesis of which may be regulated by modulation of the nicotinic acetylcholine receptor which comprises a biologically acceptable carrier or diluent and an effective amount of a compound of the following formula effective to treat a patient suffering from the condition or disease:

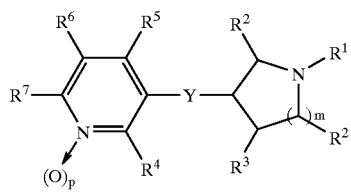

wherein
m is selected from 0, 1 or 2;
p is selected from 0 or 1;
Y is selected from the group consisting of O, S, S(O) and $S(O)_2$;

$R^1$ is independently selected from the group consisting of H—, HO—, O—, $C_{1-6}$alkyl—, $C_{2-6}$alkenyl—, $C_{2-6}$alkynyl—, $C_{3-6}$cycloalkyl$C_{1-3}$alkyl—, phenyl$C_{1-3}$alkyl—, —C(O)$C_{1-6}$alkyl, —C(O)phenyl, —C(O)$C_{1-6}$alkylphenyl, —C(O)O$C_{1-6}$alkyl, —C(O)Ophenyl, —C(O)NH$C_{1-6}$alkyl, —C(O)N($C_{1-6}$alkyl)$_2$ and —C(O)NHphenyl; wherein $R^1$ is optionally substituted on a carbon atom with one to three $R^a$ substituents; wherein $R^a$ is independently selected from the group consisting of $C_{1-4}$alkyl, $C_{1-4}$alkoxy, hydroxy$C_{1-4}$alkyl, carbomethoxy, acetoxy, nitro, Cl, Br and F;

$R_2$ is independently selected from the group consisting of H, $C_{1-6}$alkyl, phenyl and heteroaryl; wherein heteroaryl is as defined below;

$R^3$ is selected from the group consisting of H, $C_{1-6}$alkyl, Cl, Br and F; with the proviso that if m is 0, then $R^3$ is not Cl, Br or F; and $R^4$, $R^5$, $R^6$ and $R^7$ are independently selected from the group consisting of hydrogen and at least one is a selected radicals; wherein the radicals are selected from the group consisting of:

g) a sulfur radical: —(S=(O)$_n$)—$R^s$; wherein n is selected from 0, 1 or 2 and $R^s$ is as defined previously;
$R^s$ is a group selected from the group consisting of $C_{1-4}$alkyl, phenyl and heteroaryl (each of which is optionally mono- or di-substituted with $R^q$, as defined previously); wherein
heteroaryl is a monocyclic aromatic hydrocarbon group having five or six ring atoms, having at least one carbon atom which is the point of attachment, having from one to three carbon atoms replaced by N in the case of six ring atoms, having one carbon atom replaced by O, S or N in the case of five ring atoms and, optionally, having up to three additional carbon atoms replaced by N;
$R^q$ is selected from the group consisting of —OH, —OCH$_3$, —CN, —C(O)NH$_2$, —OC—(O)NH$_2$, CHO, —OC(O)N(CH$_3$)$_2$, —SO$_2$NH$_2$, SO$_2$N(CH$_3$)$_2$, —SOCH$_3$, SO$_2$CH$_3$, —F, —CF$_3$, —COOM$^a$ (wherein M$^a$ is selected from the group consisting of hydrogen, alkali metal, methyl and phenyl), tetrazolyl (wherein the point of attachment is the carbon atom of the tetrazole ring and one of the nitrogen atoms is mono-substituted by M$^a$, as defined previously) and —SO$_3$M$^b$ (wherein M$^b$ is selected from the group consisting of hydrogen and an alkali metal);

h) a sulfamoyl group: —SO$_2$N(R$^y$)R$^z$; wherein R$^y$ and R$^z$ are as defined previously;

$R^y$ and $R^z$ are independently selected from the group consisting of H, $C_{1-4}$alkyl (optionally mono- or di-substituted by $R^q$, as defined previously), a three to five membered diradical to form a ring wherein $R^y$ and $R^z$ are fused (optionally mono- or di-substituted with $R^q$, as defined previously) and a two to five membered diradical interrupted by —O—, —S—, —S(O)— or —S(O)$_2$— to form a ring wherein $R^y$ and $R^z$ are fused (optionally mono- or di-substituted with $R^q$, as defined previously);

n) a sulfonamido group: —(N—$R^t$)SO$_2$$R^s$; wherein $R^s$ and $R^t$ are as defined previously;
$R^t$ is selected from the group consisting of H and $C_{1-4}$alkyl; wherein the alkyl chain is optionally mono- or di-substituted by $R^q$, as defined previously;

v) a thiocarbamoyl group: —(C=S)N($R^y$)$R^z$; wherein $R^y$ and $R^z$ are as defined previously;

x) a thiocyanate radical: —SCN;

y) a trifluoromethylthio radical: —SCF$_3$;

z) a tetrazolyl radical; wherein the point of attachment is the carbon atom of the tetrazole ring and any one nitrogen atom is mono-substituted by a substituent selected from the group consisting of hydrogen, an alkali metal and a $C_{1-4}$alkyl radical; wherein the $C_{1-4}$alkyl radical is optionally mono- or di-substituted by $R^q$, as defined previously;

ac) a $C_2$–$C_4$ alkenyl radical; wherein the radical is mono-substituted by a substituent selected from the group consisting of any one of g), h), n), x), y) and z) or is mono-substituted by substituents selected from the group consisting of phenyl, pyridyl, quinoline and isoquinoline; wherein each phenyl, pyridyl, quinoline or isoquinoline substituent is optionally mono- or di-substituted by $R^q$, as defined previously;

ae) a $C_1$–$C_4$ alkyl mono-substituted by a substituent selected from the group consisting of any one of g), h), n), x), y) and z);

ag) a $C_2$–$C_4$ alkynyl radical; wherein the radical is mono-substituted by a substituents selected from the group consisting of any one of g), h), n), x), y) and z) and trialkylsilyl;

ah) phenyl radicals ai) bicyclic radicals; wherein the radical is independently selected from the group consisting of naphthyl, biphenyl, quinoline, indolizine, indole, isoindole, indoline, benzofuran, indazole, benzimidazole, purine, quinolizine, cinnoline, quinoxaline, phthalazine and quinazoline;

aj) heterocyclic radicals; wherein the radical is independently selected from the group consisting of furyl, thienyl, pyrazinyl, pyridazinyl, pyrimidinyl, pyrrolyl, pyrazolyl, imidazolyl, indolyl, thiazolyl, oxazolyl, thiadiazolyl, oxadiazolyl, quinolinyl and isoquinolinyl; and ak) aryl and heteroaryl radicals; wherein the radical is independently selected from the group consisting of any one of ah) through aj); wherein the radical is substituted with one or two substituents independently selected from the group consisting of $C_1$–$C_6$ alkyl, $C_1$–$C_6$ haloalkyl, $C_1$–$C_6$ alkoxy, $C_1$–$C_6$alkoxy$C_1$–$C_6$alkyl, $C_1$–$C_6$alkoxy$C_1$–$C_6$alkoxy, $C_1$–$C_6$ thioalkyl, halogen, cyano, hydroxy, amino, nitro and $C_1$–$C_6$alkylamino, in which any terminal carbon atom may be replaced by a group selected from the group consisting of carboxyl and $C_2$–$C_6$alkoxycarbonyl;

and pharmaceutically acceptable salts and esters thereof.

22. The pharmaceutical composition of claim 21 wherein the condition is acute or chronic pain and the patient is in need of analgesia.

23. The pharmaceutical composition of claim 21 wherein the condition or disease is Alzheimer's disease, memory loss or dementia or loss of motor function.

* * * * *